United States Patent [19]

Skinner et al.

[11] Patent Number: 5,219,567
[45] Date of Patent: Jun. 15, 1993

[54] VACCINE AGAINST HERPES VIRUSES

[75] Inventors: Gordon R. Skinner, Solihull; Alexander Buchan, Birmingham, both of Great Britain

[73] Assignee: The University of Birmingham, Birmingham, England

[21] Appl. No.: 495,710

[22] Filed: Mar. 19, 1990

Related U.S. Application Data

[60] Continuation-in-part of Ser. No. 213,269, Jul. 29, 1988, abandoned, which is a division of Ser. No. 478,333, Mar. 24, 1983, Pat. No. 4,816,250.

[30] Foreign Application Priority Data

Mar. 24, 1982 [GB] United Kingdom ............... 8208650

[51] Int. Cl.$^5$ ...................... A61K 39/12; C12N 7/00
[52] U.S. Cl. ................... 424/89; 435/235.1; 435/237; 435/238
[58] Field of Search ............... 424/89; 435/235.1, 237, 435/238

[56] References Cited

U.S. PATENT DOCUMENTS 4,374,127  2/1983  Larson et al. .................. 424/89
4,452,734  3/1980  Larson et al. .................. 424/89

FOREIGN PATENT DOCUMENTS 0001365  9/1978  European Pat. Off. .
2037165  12/1979  United Kingdom .

OTHER PUBLICATIONS

Muramatsu, "Isolation of Nuclei and Nucleoli", "Cell Physiology IV", 1981, pp. 195-228.
Alberts et al, "Molecular Biology of the Cell", Garland Publishing Company, New York, 1983, p. 145.
Glauret, "Practical Methods in Electron Microscopy", North-Holland Publishing Company, Amsterdam, 1975, p. 44.
Heide et al, "Plasma Protein Fractionation", "The Plasma Proteins", vol. 3, Academic Press, New York, 1977, pp. 548-550.
Harris, "Techniques In Experimental Virology", Academic Press, 1964, p. 157. .
Skinner et al., "The Preparation, Efficacy . . . in Human Subjects", Medical Microbiology and Immunology, V. 169, p. 39-51, (1980).
Pearson et al., "Isolation of Virus-free . . . Membrane Vesicles", Proc. Natl. Acad. Sci., v. 74, p. 2546-2550 (1977).
Skinner et al., "Immunogenicity and Protective . . . Infection", Br. J. exp. Path., vol. 63, No. 2, p. 378-387 (1982).
Skinner et al., "Preparation and Immunogenicity . . . Genitalis", Br. J. Vener. Dis., vol. 58, No. 6, p. 381-386 (1982).
Skinner et al, *Med. Microbiol. Immunol.*, vol. 169, pp. 39-51, 1980.
Heide et al, *Plasma Protein*, vol. 3, pp. 545-595, 1977.

Primary Examiner—Michael G. Wityshyn
Assistant Examiner—Abdel A. Mohamed
Attorney, Agent, or Firm—Leydig, Voit & Mayer

[57] ABSTRACT

A vaccine against a herpes virus is prepared by infecting cells with virus, separating the nuclei of the infected cells from their cytoplasmic fraction, discarding the nuclei, fixing the polypeptide chains of the virus antigens in the cytoplasmic fraction, and precipitating those antigens, the precipitated antigens providing the active constituent of the vaccine. A characteristic strain of the virus may be used, so that vaccinated subjects can be distinguished from infected subject.

15 Claims, 1 Drawing Sheet

VACCINE AGAINST HERPES VIRUSES

This application is a continuation-in-part of our co-pending application Ser. No 213,269, filed Jul. 29 1988, which in turn is a divisional of application Ser. No. 478,333, filed Mar. 24 1983 and now issued as U.S. Pat. No. 4,816,250.

The herpes virus group includes herpes simplex viruses (HSV), cytomegalovirus (CMV), varicella zoster virus (VZV), Epstein-Barr virus (EBV) and herpes B virus of monkeys, for all of which human beings can act as a natural host. Other herpes viruses have as natural host the frog, chicken, mouse, guinea pig, cat, dog, swine, cow, horse and monkey. All members of the herpes virus group are relatively large DNA viruses and share a common structure comprising double stranded DNA surrounded by a shell in the form of a regular icosohedron which is defined by 162 radially extending capsomeres. The capsomeres are in the form of elongate hollow prisms some of which are hexagonal and some pentagonal in cross section. The shells of herpes viruses are normally surrounded by an ether-sensitive glycoprotein envelope, some of the glycoproteins being antigenic. All herpes viruses replicate in essentially the same manner in the nuclei of cells. Virus nucleic acid is synthesised in the cell nucleus, while virus proteins are synthesised in the cytoplasm of the infected cell. Some of these virus proteins remain in the cell cytoplasm, while others move to the cell nucleus It has been shown by Ludwig et al, IARC Sci Publ 1978, 235-241, that herpes viruses which are only distantly related in their genetic material and which cause diseases in different natural hosts, share a common glycoprotein antigen.

It has been proposed, for example in British patent 2037165, to prepare a vaccine against infection by, inter alia, herpes viruses.

Viral vaccines are generally prepared from virus introduced into host animal cells which are cultured in animal fluids e.g. serum. Certain herpes viruses such as HSV and EBV are suspected of being oncogenic in human beings. In order to be satisfactory, any vaccine produced from a herpes virus under suspicion should therefore include a minimum achievable quantity of viral genetic material. Preferably the amount of viral DNA in a standard dose (300 micrograms of protein) should not exceed 30 picograms.

Though the specific example described hereafter discloses preparation of a vaccine against HSV, the same preparation technique has been used to obtain vaccines against VZV and CMV. Evidence from research data indicates that the method described would be effective to derive a satisfactory vaccine from any herpes virus.

A variety of methods have been proposed for reducing virus DNA in a vaccine produced therefrom. U.S. Pat. No. 4,374,127 teaches addition of DNase to an infected cell extract which has been subjected to treatment which will have homogenised the infected cells. Though the resulting cell material may be free from intact DNA it will necessarily contain fractionated DNA, virus particles and proteins from the cell nuclei, as well as DNase. The above reference also teaches that the required virus glycoproteins are subsequently separated by means of a lectin sepharose column. This last step will inevitably reduce the yield of the desired antigens.

It has been proposed by Skinner et al in "The preparation, efficacy and safety of 'Antegenoid' vaccine NFU$_1$(S$^-$L$^+$) MRC toward prevention of herpes simplex virus infections in human subjects" Med Microbiol Immunol 169,39-51 (1980) to disrupt the infected cell material before adding a surfactant which strips antigenic proteins from the cell membranes and virus envelopes. This reference teaches that formaldehyde is subsequently added in an attempt to inhibit biological activity of host cell and virus DNA which will necessarily have been released by the disruption step. The formaldehyde treatment could leave a substantial amount of cell and virus DNA, which was appreciated by Skinner et al and was the reason for treatment of the host cells with an antiviral agent, for example lithium chloride, before infection. Lithium treatment will necessarily inhibit replication of virus particles in the infected cells and inevitably reduce the amount of newly synthesised glycoproteins in the infected cells and virus particles.

British patent 2037165, referred to above, also disclosed subjecting infected cell material to a surfactant at a concentration, and for a time and temperature which will result in cell disruption. The resulting material is then reacted with an anti-HSV serum to provide an antigen-antibody reaction. The resulting immunocomplex constitutes the vaccine. Such a method will result in a low yield of vaccine and does not lend itself to large scale commercial production.

SUMMARY OF THE INVENTION

It is an object of the invention to provide a herpes vaccine which can be produced on a large commercial scale, which has a low viral DNA content and whose administration is unaccompanied by antibody reaction of the subject to host cell or culture medium used in vaccine preparation.

The present invention discloses a method of preparing a vaccine against a herpes virus, whereby the infected cell material is subjected to surfactant treatment which is such that the nuclei of infected host cells, which contain over 99% of the virus DNA, are separated intact from the cell cytoplasm. The cell nuclei may readily be removed and discarded by means of low speed centrifugation. The polypeptide chains of the glycoproteins in the cytoplasmic fraction are fixed and precipitated, the precipitate providing the active constituent of the required vaccine.

In one of its embodiments the present invention relates to a vaccine against HSV which is prepared from a selected virus strain having a known, unique and readily recognisable distribution of proteins of particular molecular weights. The use of such a vaccine produces, in a vaccinated subject, antibodies whose molecular weight groupings correspond to those of the virus strain, and will enable subsequent determination whether any antibodies present have arisen as a result of infection or from vaccination.

Embodiments of the invention will now be described by way of example only and with reference to a vaccine against a Herpes simplex virus strain whose characteristics are shown by the accompanying drawings in which:

DESCRIPTION OF THE PREFERRED EMBODIMENTS

Herpes simplex virus is a relatively large virus consisting of (1) a nucleoprotein 'core' measuring 75 mu in diameter containing double-stranded deoxyribonucleic acid (DNA); (2) a capsid with icosahedral symmetry consisting of 162 capsomeres and, in a certain proportion of particles, (3) a glycoprotein-containing lipoprotein envelope.

An infected cell material is incubated using MRC5 cells, a human embryonic cell line. MRC5 cells are at present the preferred cells, and in some cases their use is mandatory. These cells are, however, slow growing, and recently the possibility has been considered that vaccines obtained by their use could result in a vaccinated person developing an immune reaction to other human tissue, thereby introducing the possibility of rejection of any subsequent tissue transplant. Embodiments of the processes presently described include steps by means of which the cell proteins may be removed and will thereby no longer be able to elicit an immune response. Additionally, removal of the cell protein should overcome various objections to the use of cell lines other than MRC5.

For the described example the MRC5 cells are obtained from the National Institute for Biological Standards and Controls, Hampstead, England. These cells are cultivated in Eagle's medium supplemented with 10% foetal or newborn calf serum and 10% tryptose phosphate broth to growth in rotating Winchester bottles (2,500 ml) which normally entailed 3-4 passages. The foetal calf serum is obtainable from Sera-Lab. Plasma Laboratory Limited, Crawley Down, Sussex, England. Tryptose phosphate broth is obtainable from Difco Laboratories, West Molesey, Surrey, England, and sterilized by auto-claving. Aliquots of the cultivated cells are stored in a glycerol-containing medium at $-70°$ C. for subsequent use.

The cells are allowed to reach near confluence as sheets within 2,500 ml rotating Winchester bottles. Each cell sheet is subsequently washed with prewarmed Eagles's medium to remove the foetal calf serum. The cells are maintained in a serum-deprived condition for 24 hours. Serum deprivation will tend to result in a significant reduction in the level of virus antigens. Though serum deprivation has previously been considered necessary in order to reduce the level of calf serum in the resulting vaccine, it is envisaged that at least some of the steps described thereinafter, of precipitating virus proteins from the infected cell extract, may allow the serum deprivation step top be omitted entirely, whereby the virus antigen yield may be substantially increased.

Figure 1:
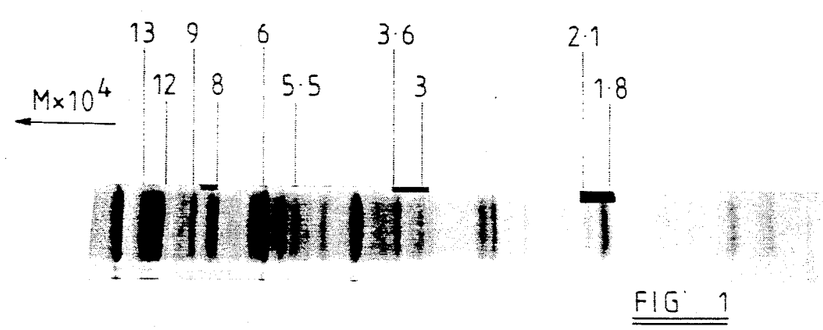
FIG. 1 shows the electrophoretic distribution of the molecular weights of characteristic proteins of the virus.
Figure 2:
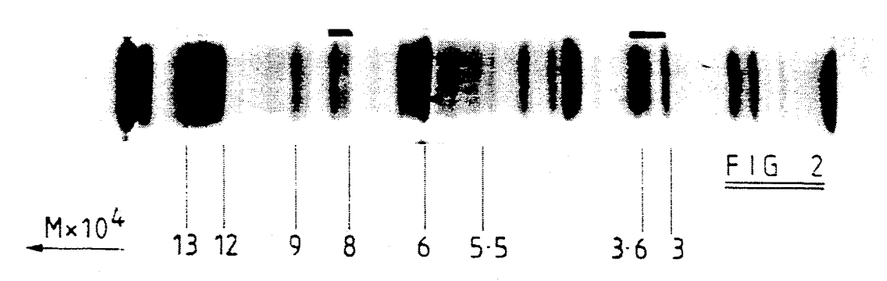
FIG. 2 is an expanded electrophoretic distribution of part of FIG. 1.

After the 24 hours of serum deprivation the cells are washed with prewarmed Eagle's medium and infected with Herpes simplex virus type 1 (HSV1). The virus used is the Troisbell strain developed in the Department of Medical Microbiology of the University of Birmingham, England. The virus was isolated from an oral cold sore of an otherwise healthy middle-aged subject, and identified as HSV1 by neutralisation kinetics, agar gel diffusion tests, and by polypeptide analysis using polyacrylamide gel electrophoresis. The patterns obtained by gel electrophoresis are shown in FIGS. 1 and 2 and will be described in detail hereafter. The strain was isolated in human embryonic lung tissue and subsequently cloned three times by limit dilution in a preparation of the MRC5 cells previously referred to. This preparation comprised MRC5 cells cultivated in Eagle's medium containing gamma-irradiated foetal calf serum. The cloned virus was isolated and identified as HSV1 by the methods indicated above, which were used for the original identification.

The Troisbell virus strain is added to the serum-deprived cells at a multiplicity of five plaque-forming units per cell. Virus adsorption is contained for one hour at 37° C. following which the cells are again washed with prewarmed Eagle's medium and re-incubated.

It has been found that after 24 hours of incubation the cytopathic level of the incubated material os 100%. At this stage each cell sheet is again washed with Eagle's medium and removed from its Winchester bottle. The cells are then suspended in phosphate buffered saline to a concentration of $4 \times 10^7$ ml. The suspended cells are then subjected to surfactant treatment at a concentration, and for a time and temperature which will separate the cell nuclei from their cytoplasmic fraction, but are insufficient to disrupt the nuclei. Nonidet NP40 detergent, obtainable from BDH Chemicals, of Poole, England, and having the product designation 56009, is added, to a final concentration of 1% by volume, and maintained thus at not higher than room temperature (15°–20° C.) for 10 minutes. The process has been found to be more readily controllable at a temperature of 4° C. The action of the detergent is to part the nuclei of the cells from their cytoplasm and to strip important antigenic proteins from enveloped virus particles in the cytoplasm. The detergent also reduces, but may not totally eliminate, the infectivity of those virus particles.

The resulting preparation is centrifuged at about 650 g for 10 minutes and the supernatant, which is the cytoplasmic fraction of the preparation, is collected, the remaining material being discarded. The supernatant at this stage contains virus antigenic proteins and virus particles, human embryonic cell proteins, and proteins from the foetal calf serum, as well as small amounts of extra-particulate virus DNA, together with Nonidet detergent.

The polypeptide chains in the cytoplasmic fraction are stabilized using a known fixing agent such as formaldehyde or glutaraldehyde, to a final concentration of 0.04%. In addition to fixing the polypeptide chains this step inactivates any residual virus and cell DNA and reacts with the virus particles to inactivate any residual virus nucleocapsids.

The resulting fraction is then centrifuged over a cushion of sucrose at a concentration of 20% W/V for 5 hours at $10^5$ g, in a wide bucket of 40 ml volume. The sucrose in Grade 1 and is obtainable from Sigma Biochemicals, Poole, England, under the product designation 59378. The 4 ml top fraction in each centrifuge container comprises a purified cytoplasmic fraction which has been found to contain no virus particles or virus nucleic acid, and to consist of virus proteins, together with cell and serum proteins, as well as the formaldehyde, sucrose and detergent previously added.

The purified cytoplasmic fraction is then subjected to a process which precipitated the virus protein from the fraction, either alone or in combination with antibodies to the protein. This precipitation may be accomplished by the following steps, or combinations of steps:

(i) The purified cytoplasmic fraction is passed through an activated sepharose column to which antibodies to the MRC5 cell proteins are covalently bound.

The sepharose column may also include antibodies to the foetal calf serum in which the MRC5 cells are incubated. Alternatively the top fraction may be passed through successive activated sepharose columns, to remove any proteins other than the virus antigens.

The foregoing step or steps, cause the unwanted proteins to form antigen/antibody complexes which remain within the column and, as indicated above, enables cell lines other than MRC5 to be used for vaccine preparation and also enables the serum deprivation step to be reduced in duration, or possibly to be eliminated.

(ii) Preferably after removal of the unwanted proteins, aluminium hydroxide adjuvant is added to the preparation and entrains the virus antigens as a washable suspension. The resulting mixture is agitated at room temperature for one hour and subsequently centrifuged at low speed to separate the antigen/adjuvant suspension. The supernatant, containing the Nonidet detergent fixing agent (e.g. formaldehyde) and sucrose is discarded and the separated suspension is washed in sterile phosphate-buffered saline and forms the required vaccine.

In addition to enabling the virus antigens to be selected out, the aluminium hydroxide suspension permits washing to remove all traces of the supernatant. The volume of aluminium hydroxide required is a small proportion of the volume of the preparation which is added to it. Large amounts of the preparation may therefore be treated in a container which is not substantially larger than the volume of the preparation currently passing through this step.

The aluminium hydroxide acts as an adjuvant which enhances the effectiveness of the resulting vaccine, and the suspension is readily stored.

(iii) Alternatively, aluminium hydroxide adjuvant is added directly to the purified cytoplasmic fraction, to entrain the virus antigens and proteins from the MRC5 cells as a washable suspension, the mixture being treated as in step (ii) above, to provide the vaccine.

(iv) The purified cytoplasmic fraction is alternatively reacted with antibodies to the viral proteins, to provide an antigen/antibody precipitate which is separated from the remainder of the material by centrifugation. The separated precipitate is washed in phosphate-buffered saline to remove all traces of Nonidet, fixing agent, sucrose of MRC5 cell protein, this precipitate forming the required vaccine. If desired aluminium hydroxide may be added to the precipitate, as an adjuvant only.

(v) In another alternative step a suitable organic solvent which reduces the dielectric constant of the water and thereby allows precipitation of the proteins in the fixed cytoplasmic fraction, is added to that fraction and precipitates the proteins therein. Acetone, ethanol and methanol are examples of such solvents and are added at temperature between 0° C. and −30° C., at a ratio of 10 parts of solvent to 1 part of water in the cytoplasmic fraction. Preferably the solvent temperature is between −10° C. and −20° C. The precipitate is separated by centrifugation and the remaining solvent on the precipitate is evaporated off. The precipitated proteins are then either re-suspended in phosphate-buffered saline or added to aliminium hydroxide adjuvant.

Since this step precipitates all the proteins in the purified cytoplasmic fraction, it is desirable that proteins from the calf serum used at an earlier stage shall previously have been removed. If an organic solvent is used to effect protein precipitation, it is therefore preferable to have subjected the MRC5 cells to serum deprivation, as described above, before infection with the virus.

The electrophoresis gel patterns of the Troisbell HSV1 virus used for preparation of the vaccine are shown in FIGS. 1 and 2, in which molecular weights M are shown as values $\times 10^4$, and in which FIG. 2 is an expansion of part of FIG. 1, obtained by the use of a different gel. In addition to identifying the virus strain as HSV1, by virtue of molecular weight patterns which are common to all HSV1 strains, these gel patterns exhibit characteristics which will readily be recognised by one skilled in the art as being unique, and will enable identification of the Troisbell strain. Particularly characteristic of the Troisbell virus are the protein groups at molecular weights between $8 \times 10^4$ and $9 \times 10^4$, and between $3 \times 10^4$ and $3.6 \times 10^4$. Moreover these groupings, takin in conjunction with groupings between $1.8 \times 10^4$ and $2.1 \times 10^4$, between $5.5 \times 10^4$ and $6 \times 10^4$ and between $12 \times 10^4$ and $13 \times 10^4$, define a unique pattern which will enable identification of the Troisbell virus, vaccines derived therefrom, and of antibodies produced by vaccinated subjects. Use of this vaccine will thereby render it possible to determine whether the presence in a subject of antibodies to HSV1 is attributable to vaccination or to infection.

Samples of the Troisbell virus strain were deposited on Mar. 22, 1983 at the Collection National de Cultures de Micro-organisms, Paris, France, which is an International Depository under the Budapest Convention, under the Accession No I-224. A Certificate of Viability was issued on Sep. 15, 1983. Further samples of the Troisbell strain were deposited on Dec. 11, 1986 at the Public Health Laboratory Service, Centre for Applied Microbiology and Research, Porton Down, England, which is also an International Depository under the Budapest Treaty, under the Accession No V86121102. Additional stocks of the Troisbell virus strain are held in the Department of Medical Microbiology of the University of Birmingham, England, under conditions intended to ensure indefinite viability and replacement of any samples which may be reported by either International Depository as not viable. The above Department has undertaken to provide bona fide requests for samples of the virus, on the same basis as the International Depositories.

Extensive tests have been carried out on vaccines against herpes simplex produced by a method described in this application. These tests include those performed to obtain results for submission to the US Food and Drug Administration who have authorised clinical trials of the subject vaccine on human subjects.

Autoradiographs were prepared of purified DNA from HSV, at successive dilutions, as well as autoradiographs of an anti-HSV vaccine according to the present invention. Subsequent scanning of the autoradiographs by a Joyce-Loebel Integrating Densitometer showed that the DNA content of the vaccine was between 1.5 and 2.4 picograms per 300 microgram dose. This figure is clearly well within the desired upper limit of 30 picograms, and is believed not to have been attained with any other herpes vaccine.

Results of clinical trials on human subjects of a HSV vaccine according to the present invention have been reported as follows:

Muniu et al "Antibody reactivity with Skinner HSV vaccine" Med Microbiol Immunol (1987) 176:315–327, which shows development of antibody reactivity to HSV in vaccinated subjects, unaccompanied by HSV infection or antibody reactivity to host cell or culture medium used in vaccine preparation.

More particularly, Muniu et al. investigated antibody reactivity in vaccinated subjects against type 1 and type 2 HSV, bovine mammillitis virus (BMV), rubella virus and against host cell MRC-5 and calf serum antigen.

Study Population. Prior to and following vaccination, sera were obtained form subjects (consorts) who were the sexual partners of patients with recurrent herpes genitalis but had no history of herpes genitalis or oral cold sores. The study groups were considered in terms of the result of conventional neutralization tests against type 1 or type 2 HSV; subjects whose sera showed no significant neutralization were assigned to the sero-negative group and subjects whose sera showed significant neutralization to the "sero-positive" group.

Vaccine. Vaccine was prepared as previously described by Skinner GRB, Woodman CGH, Hartley CE, Buchan A, Fuller A, Durham J, Synmott M. Clay JC, Melling J, Wiblin C, Wilkins J, (1982) "Preparation and Immunogenicity of Vaccine AcNFU (S−) MRC Towards the Prevention of Herpes Genitalis", Br J Vener Dis, 58:381–386; (1982): and Skinner GRB, Buchan A, Hartley CE, Williams D, Wilbanks G, Turyk M, Nankoong D (1982) "Immunogenicity and Efficacy of Vaccine $AcNFU_1(S-)$ MRC in a Rhesus Monkey Model Towards Protection Against Primary Herpes Genitalis", Br J Exp Pathol, 3:378–382 except that whole infected MRC-5 cells instead of disrupted infected cell extract was treated with Nonidet, permitting removal of cell nuclei prior to further steps in vaccine preparation. In brief, therefore, the vaccine was a detergent-treated, particle-free cytoplasmic extract of type-1 HSV (troisbel) infected human embryo lung cells (MRC-5). The vaccine contained less than 50 pg viral DNA per vaccine dose (0.3 mg protein) with a fragment size of less than 100 bases as determined by agarose gel analysis; the vaccine contained all the poly-peptides synthesized by virus-infected cells including glycoprotein D (gD) which was present at a concentration of at least 0.6 μg per vaccine dose.

Vaccination schedule. Each subject received three subcutaneous vaccinations into the posterior aspect of the upper arm at 3-weekly intervals. Each vaccine dose contained approximately 300 μg of protein; vaccine was administered with "Alhydrogel" adjuvant.

Viruses. HSV strain "HFEM" and strain "3345" were used as prototype type 1 and type 2 strain respectively for all immunological tests. Virus strains were stored at −70° C. until use.

Sera. Human sera were obtained prior to and 2 weeks after vaccination. The sera were inactivated by heating at 56° C. for 30 minutes and stored at −20° C.

Antigen for radio-immune assay. Type 1 or 2 antigen was prepared in baby hamster kidney cells (BHK-21). The cells were removed, centrifuged at 1,000 rpm for 10 min, washed in phosphate-buffered saline and suspended in (PBS) to $5 \times 10^7$ cells per ml. The cells were then dissolved in 1% Nonidet P40 for 24 h. The antigen was dialyzed and disrupted by ultrasonic vibration and inactivated with 0.04% formaldehyde at 37° C., centrigued at low speed nad stored at −70° C. The antigens were titrated against type 1 and type 2 HSV immune rabbit sera given an optimum working dilution of 1/600 of each antigen. Uninfected BHK-cell antigen was included in every assay.

Antigen for Western blotting analysis. Type 1 and type 2 antigen was prepared in GHK-cells infected with 20 pfu/cell respectively. The infected cells were washed in DA and dissolved in 1 ml of solution containing 2% sodium dodecyl sulphate, 5% 2-mercaptoethanol and 3% sucrose in 0.05 m - Tris - HCl (pH 7.0). BHK uninfected cell extract antigen was included for control purposes and an $^{35}S$ methionine-labelled type 1 infected cell extract was included in each gel as marker.

Antigens for immunodiffusion. These were prepared from BHK-21 cell layers infected using high multiplicity (20 pfu/cell) of each virus. The infected cells were removed, centrifuged, washed in DA and resuspended in water at a concentration of $1 \times 10^8$ cells/ml. The antigen was disrupted by ultrasonic vibration centrifuged and stored at −70° C.

Conventional neutralization test. Samples of type 1 or type 2 ($5 \times 10^5$) pfu/ml) HSV were mixed with equal volumes of an appropriate dilution of the heat inactivated pre-vaccination or post-vaccination serum at 25° C. for 60 min. Surviving virus was assayed in BHK-21 cells and the $\log_{10}$ reduction in virus titre was determined for each serum as follows:

$$\text{Log}_{10} \text{ reduction} = \log_{10} V_o - \log_{10} V_t.$$

where $V_o$ = number of plaques with pre-immune serum at a time $V_t$ = number of plaques with test serum at time, t. Rabbit preimmune serum and a positive and negative human serum against HSV were included as controls in every test.

Augmented neutralization test. Augmented neutralization test with type 1 HSV was carried out as previously described ]4]. Briefly, equal volumes (100 μl) of type 1 HSV containing $5 \times 10^6$ pfu/ml and a 1/10 dilution in PVBS of the serum were reacted at 37° C. for 4 hours. After 4 h, an equal volume (50 μl) of the reaction mixture was reacted with an equal volume of sheep-anti-human IgG (diluted ½ in PBS) for 10 mins at room temperature. The reaction mixture was diluted and surviving virus titrated as described. Due to thermal lability of type 2 HSV, a 1 h incubation at 37° C. was used for this virus.

Radio-immune assay. The assay was carried out by a modified method from Howes et al. (J Gen Virol, 44, 81–87 (1979) in roundbottom flexible 96-well trays coated over-night with 50 μl of 1/600 dilution of the appropriate antigen. The antigen was removed and trays washed five times in PBS. Non-specific sites were blocked with 50 μl of either 100% or 50% new born calf serum (NBCS) in PBS at 37° C. for 1 h. The serum was removed, the trays washed once in PBS and 50 μl of five fold dilutions of serum added to the appropriate well for 1 h at room temperature. The serum was removed, trays washed five time in PBS and 45 μl of Protein "A" containing 30–50,000 cpm added per well. The plate was washed, cut up and counted on a gamma counter. The titre of each serum was determined from the dilution—response graph and recorded as the end point dilution which reacted to a two-fold higher level than with uninfected cell antigen.

"Western Blotting". A 7% slab gel cross linked with N'N' methylene-bisacrylamide was prepared for blotting and performed using a discontinuous buffer system. The antigens were disrupted prior to electrophoresis at 45° C. for 10 min. The electrophoresis was carried out at 150V/60 mA for 2-3 h. The electrophoresis transfer on to nitrocelulose paper strips (0.4 μl) was carried out overnight in blotting buffer containing 25 mM Tris and 192 mM glyine in 20% methanol pH 8.3. After transfer, the nitrocellulose strips were incubated in 5% BSA in 0.01% azide at 20° C. for 2 h and at 37° C. for 1 h with gentle shaking. The strips were incubated at 20° C. for 90 min in "boats" with serum diluted in 1/50+200 μg/ml ovalbumin (20 ml/strip) with fast shaking. The PBS nitrocellulose strips were washed for 1 h.

The nitrocellulose strips were reacted with $^{125}$I Protein "A" diluted in PBS in 200 μg/ml ovalbumin (20 ml/strip) to give $2 \times 10^6$ cpm/strip for 30 min in "boats" at room temperature with fast shaking. The strips were washed as previously described after serum incubation, stained in amido black and destained for 1 min. The strips were rinsed in water, dried overnight and autoradiographed using Kodak X-Mat (RP) film for 5-7 days for detection of radiolabelled polypeptides.

Immunodiffusion. Immunodiffusion tests were carried out in 1% purified agar (supplied by Oxoid Limited) containing 0.85% NaCl and 0.1% sodium azide in water. A pattern of wells equally spaced around a central well was used. Each well was filled to capacity with appropriate antigen or serum (both undiluted) and left at room temperature for 72 h. Antigens were tested against hyper-immune sera where they would give multiple precipitin lines.

Statistical interpretations. A significant naturalization or IVR antibody response was adjudged by comparision of total prevaccination and post-vaccination plaque counts which distribute in Poissonian fashion. Antibody responses on radio-immune assay were considered significant when post-vaccination end-point titres were at least four fold greater than pre-vaccination endpoint titres.

Inhibition of virus release assay (IVR assay). IVR antibody reactivity was measured as previously described by Skinner GRB, Mushi EZ, Witney JE (1976) "Immune Inhibition of Virus Release from Herpes Simplex Virus—Infected Cells, *Intervirology* 6:296-308. Monolayers of BHK-21 cells were infected in round bottom Limbro trays with 5 pfu/cell of type 1 HSV "strain troisbel". After incubation for 16 h the medium was removed, the cell sheet washed with warm medium and the serum under test added a dilution of 1:5 for 90 min at 37° C. The serum was removed, the cell sheet washed and finally replaced with 0.15 ml of medium for 5 h following which the supernatant medium was centrifuged at low speed to remove cells and the supernatant titrated for virus infectivity. The inhibition of virus release was calculated as the $\log_{10}$ virus titre in the supernatant medium of cells treated with growth medium (ETC) minus the $\log_{10}$ virus titre in the medium of cells treated with the serum under test. A known positive and negative serum were included in each test for control purposes.

RESULTS

Antibody reactivity against HSV-related antigens.

Neutralization. All but two sero-negative subjects responded to vaccination as adjudged by conventional neutralization and only one subject remained negative (against type 2 only) on testing by augmented neutralization (Tables 1 and 2). Every sero-positive subject had a significant neutralizing antibody response against both virus types by both conventional and augmented neutralization. The proportional increase in antibody levels was similar for both virus types whether tested by conventional or augmented neutralization.

TABLE 1

Antibody reactivity against type 1 HSV in vaccinated subjects

|  | No. of subjects | No. with significant response | Mean antibody level Pre-vac | Mean antibody level Post-vac |
| --- | --- | --- | --- | --- |
| Conventional neutralisation |  |  |  |  |
| Sero-negative | 9 | 7(78%) | 0.00 | 0.38 |
| Sero-positive | 6 | 6(100%) | 1.07 | 1.72 |
| Augmented neutralisation |  |  |  |  |
| Sero-negative | 5 | 5(100%) | 0.0 | 1.82 |
| Sero-positive | 10 | 10(100%) | 1.68 | 2.30 |
| Radio-immune assay |  |  |  |  |
| Sero-negative | 5 | 5(100%) | 1/5 | 1/150 |
| Sero-positive | 10 | 9(90%) | 1/750 | 1/2500 |
| Western blotting |  |  |  |  |
| Sero-negative[a] | 4 | 2(50%) | — | — |
| Sero-positive | 11 | 0(0%) | — | — |
| Immunodiffusion |  |  |  |  |
| Sero-negative | 9 | 0(0%) | — | — |
| Sero-positive | 6 | 0(0%) | — | — |
| Inhibition of virus release |  |  |  |  |
| Sero-negative | 2 | 2(100%) | 0.00 | 0.08 |
| Sero-positive | 4 | 3(75%) | 0.46 | 0.82 |

[a]Sera were recorded as "significant response" when new bands could be identified; an increase in intensity of bands was not recorded in these numbers
Neutralising antibody reactivity is expressed as $\log_{10}$ reduction in virus titre; antibody levels on radio-immune assay are expressed as end point titres as described in Methods

TABLE 2

Antibody reactivity against type 2 HSV in vaccinated subjects

|  | No. of subjects | No. with significant response | Mean antibody level Pre-vac | Mean antibody level Post-vac |
| --- | --- | --- | --- | --- |
| Conventional neutralisation |  |  |  |  |
| Sero-negative | 8 | 6(76%) | 0 | 0.33 |
| Sero-positive | 7 | 7(100%) | 0.07 | 1.1 |
| Augmented neutralisation |  |  |  |  |
| Sero-negative | 7 | 6(80%) | 0 | 0.24 |
| Sero-positive | 8 | 8(100%) | 1.16 | 1.56 |
| Radio-immune assay |  |  |  |  |
| Sero-negative | 5 | 5(100%) | 1/5 | 1/150 |
| Sero-positive | 10 | 5(50%) | 1/100 | 1/250 |
| Western blotting |  |  |  |  |
| Sero-negative | 7 | 4(57%) | — | — |
| Sero-positive | 8 | 0(0%) | — | — |
| Immunodiffusion |  |  |  |  |
| Sero-negative | 13 | 2(17%) | — | — |
| Sero-positive | 2 | 0(0%) | — | — |

Neutralising antibody reactivity is expressed as $\log_{10}$ reduction in virus titre; antibody levels on radio-immune assay are expressed as end point titres as described in Methods Radio Immune Assay. Every sero-negative subject developed antibody reactivity against both type 1 and type 2 virus antigen. Nine out of 10 and 5 out of 10 sero-positive subjects developed antibody reactivity against type 1 and type 2 virus antigen respectively. The increase in mean antibody levels were more striking for type 1 HSV (Tables 1 and 2).

TABLE 3

Antibody reactivity in Western blotting

| Pattern of reactivity | No. of Patients | Pre-Vaccination Type 1 track | Pre-Vaccination Type 2 track | Post-Vaccination Type 1 track | Post-Vaccination Type 2 track |
| --- | --- | --- | --- | --- | --- |
| "Type 1" | 4 | 4 | 0 | 4 | 4 |
| "Type 2" | 1 | 9 | 1 | 1 | 1 |
| "Type 1 and type | 7 | 7 | 7 | 7 | 7 |

TABLE 3-continued

| | Antibody reactivity in Western blotting | | | |
|---|---|---|---|---|
| | | Pre-Vaccination | | Post-Vaccination | |
| Pattern of reactivity | No. of Patients | Type 1 track | Type 2 track | Type 1 track | Type 2 track |
| 2" | | | | | |
| "No reactivity" | 3 | 0 | 0 | 1 | 0 |
| Total | 15 | 11 | 8 | 13 | 12 |

Each number represents the number of sera showing reactivity in the given track

Western Blotting. Homologous reactions were always stronger for both virus types and their corresponding antisera although the level of heterologous reaction was variable for both immune and human sera. It was also possible to identify sera which contained antibody to both virus types. Viral glycoprotein regions A/B/C (molecular weight 115k–129k), E(molecular weight 80k) and D(molecular weight 50k–60k) were identified in these sera; the major virus capsid polypeptides (molecular weight type 1, 157k, type 2, 159k) and the "immediate early" polypeptides (molecular weight 175k) were identified in immune sera but less consistently in human sera. The major DNA binding polypeptide (molecular weight 129k) was identified in the immune and human sera but could not always be easily discriminated from the glycoprotein A/B/C reaction in human sera.

Following vaccination, antibodies to the heterologous virus type were detected in all five subjects who previously showed antibody to only type 1 or only type 2; of the three subjects who were seronegative, one developed antibody to type 1 HSV following vaccination. The visual intensity of the immunological reaction was increased in the four subjects with initial type 1 reactivity only and in three of the seven subjects who showed reactivity against both virus types (Table 3).

Immunodiffusion. Prior to vaccination, immunoprecipitating antibody against type-common virus antigen, "band II" was detected in 6 subjects although in 4 of these subjects there was no diffusion line with type 2 antigen. Following vaccination, band II reactivity was detectable against type 2 virus antigen in two of these four subjects.

Inhibition of virus release (IVR assay). Two sero-negative and four sero-positive sera were tested against type 1 virus infected cells by IVR assay. There was a significant antibody responsible in five of these sera (Table 1 and 4).

Neutralization of bovine mammillitis virus (BMV). Augmented neutralization tests were carried out against the 69/1 strain of V.M.V. There was an antibody response in 7 of 15 subjects with an increase in mean antibody from 0.06 pre-vaccination of 0.22 following vaccination.

Correlation of antibody responses. As expected on account of the high proportion of positive responses, there were highly significant correlations between antibody levels as adjudged by neutralization, radioimmune assay and Western blotting analysis. The one patient who did not respond to vaccination in neutralization test to type 2 HSV was the only patient to not respond to both type 1 and type 2 in radio-immune assay (Tablets 1 and 2). The seven subjects who responded in augmented neutralization test to BMV virus responded in neutralization and radioimmune assay to HSV.

Antibody reactivity against antigens not related to HSV Host cell human embryo lung cell antigen and calf serum antigen. There was no evidence of response in radio-immune assay in any of the vaccinated subjects.

Rubella virus antigen. Radial haemolysis tests against rubella virus antigen were carried out on sera prior to and following vaccination. There was evidence of antibody to rubella virus in 13 to 15 sera; following vaccination, one of the two negative sera developed a low level of antibody against rubella; the patient, a dental practitioner, did not report any recent history or exposure to rubella virus.

Clinical response to vaccinations. The subjects were followed-up over a period of 24 to 36 months—a total of 284 "patient months". None of the vaccinated subjects reported clinical features suggestive of herpes genitalis during the period of follow-up. There were no side effects following vaccination. Woodman et al "Efficacy of vaccine AcNFU$_1$(S$^-$) MRC5 given after an initial clinical episode in the prevention of herpes genitalis" Br J Vener Dis (1983) 59:311-313, which demonstrates a reduction (85% to 31%) in recurrence of episodes of herpes in vaccinated, previously infected subjects.

In this investigation, patients were referred to the herpes simplex virus (HSV) clinic at the Queen Elizabeth Medical Centre from the sexually transmitted disease (STD) clinic of the General Hospital, Birmingham, and from general practitioners and gynaecologists within the West Midlands region. A history of herpes labialis in the patient and the existence of a regular sexual partner with a history of herpes genitalis was sought. Patients were specifically asked whether orogenital contact had occurred in the week preceding the onset of lesions when a partner had oral cold sores.

The clinical outcome is presented in two groups of unvaccinated patients; those with an initial clinical episode of herpes genitalis attending the STD clinic at the General Hospital, Stoke on Trent, and a similar group who attended the queen Elizabeth Medical Centre before the start of the vaccination program.

The diagnosis of herpes genitalis was confirmed by virus isolation in all cases. When a patient was not seen at the HSV clinic during the acute period the isolate was obtained, if still available, for the regional reference laboratory for typing. Isolates were typed by kinetic neutralization tests and polyacrylamide gel electrophoresis.

Vaccination Schedule

Patients received there subcutaneous inoculations of vaccine Ac NFU$_1$ (S$^-$) MRC 5 in the region of the deltoid muscle at monthly intervals. The vaccine dose of $5 \times 10^7$ cell equivalents was administered in sterile phosphate buffered saline without adjuvant. At each clinic visit after the initial vaccination any local reaction at the site of inoculation was recorded and specific injury made about the occurrence of any lower genital tract symptoms suggesting herpetic infection. Patients were seen at 1, 3, 6 and 12 months after the last vaccination. Any patient defaulting from their follow up visit was contacted by the responsible clinician, by telephone where possible. In addition, patients were asked to contact the clinic if they suspected a further episode of herpes genitalis.

Vaccine Preparation

Subunit antigenoid vaccine was prepared as previously described. In brief, human embryo lung cells (MRC 5) obtained from the National Institute of Biological Standards were infected with herpes simplex virus type 1 strain (troisbell) and the infected cell extract treated with non-ionic detergent and formaldehyde. Virus particles were removed by ultracentrifugation and virus proteins constituting the final vaccine preparation were precipitated with cold acetone.

The safety, immunogenicity, and protective efficacy of vaccine preparations have been previously reported. Before inoculation into human subjects, vaccine batches were tested by subcutaneous inoculation of 0.05 ml ($5 \times 10^6$ cell equivalents) into the dorsal skin of newborn mice.

RESULTS

The vaccinated group comprised 15 women and seven men with a mean age of 21 (range 17 to 31) years. Five patients had a regular sexual partner who had a known history of recurrent herpes genitalis. Six patients reported orogenital contact with a partner who had had oral cold sores in the week preceding the initial clinical episode. The unvaccinated group comprises 16 women and 4 men with a mean age of 22 (range 18 to 36) years.

Virus Typing

In vaccinated patients 15 of 22 isolates were available for typing, six of which were found to be type 1 and nine type 2. The virus isolates from five patients thought to have contracted the infection as a result of orogenital contact were found to be type 1. In unvaccinated patients 11 of 20 isolates were available for typing, four of which were found to be type 1 and seven type 2.

Clinical Outcome

The table indicates the frequency of recurrent disease in relation to virus type in vaccinated and unvaccinated patients. Seven of 22 patients vaccinated after the initial clinical episode had a total of eight recurrences after a mean follow up period of 12 (range 10 to 16) months. Two recurrences preceded the third vaccination and the remainder were 1¼, 2, 6, and 7 months after the final vaccination. Two of these episodes were confirmed by clinical assessment and the virus was isolated on one occasion; the remainder were reported by the patient at the next clinic visit. Seventeen of 20 unvaccinated patients reported a total of 51 recurrences of herpes genitalis within a mean period of eight months (range three to 16 months) after the initial clinical episode.

Subjects in study. Vaccination was offered to 50 subjects who did not have a history of herpes genitalis but whose regular sexual partner had a history of the disease. The sociodemographic features of these 50 subjects are indicated in Table 1. The incidence of previous infections disease is shown in Table 2; 10 subjects (20%) had a history of recurrent oral cold sores and 1 subject had a history of recurrent ocular herpes infection. The high frequency of a history of nonspecific urethritis and condylomatous infection was of interest and merits comparison with the corresponding frequency of these infections in the general population. The pattern of recurrent herpetic disease int he index case of the 50 consorts was recorded in terms of the features indicated in Table 3.

TABLE 1

| Socio-demographic variables of subjects at risk | |
|---|---|
| Number of subjects | 50 |
| Number of males | 30 |
| Number of females | 20 |
| Age (years): | |
| Range | 18–49 |
| Mean | 30.7 (±1.04) |
| Social class: | |
| I/II | 23 |
| III | 15 |
| IV/V | 1 |
| Material status: | |
| Single | 30 |
| Married | 12 |
| Marital dissolution | 8 |
| Race: | |
| Caucasian | 49 |
| Negroid | 1 |

TABLE 2

| Other infectious diseases in subjects at risk | |
|---|---|
| | Number |
| Chickenpox | 37 |
| Herpes labialis | 10 |
| Herpes ocularis | 1 |
| Candidiasis | 15 |
| Glandular fever | 10 |
| Non-specific urethritis | 9 |
| Condylomata | 7 |
| Gonorrhoea | 3 |
| Trichomoniasis | 1 |
| Syphilis | 1 |

TABLE

| | Recurrent episodes of herpes genitalis in relation to virus type in vaccinated and unvaccinated patients | | | | | |
|---|---|---|---|---|---|---|
| | Vaccinated patients | | | Unvaccinated patients | | |
| Virus type isolated | Total No | No of patients developing recurrences | No of recurrent episodes | Total No | No of patients developing recurrences | No of recurrent episodes |
| HSV 1 | 6 | 2 | 3 | 4 | 3 | 9 |
| HSV 2 | 9 | 2 | 2 | 7 | 6 | 19 |
| Not typed | 7 | 3 | 3 | 9 | 8 | 23 |
| Total | 22 | 7 | 8 | 20 | 17 | 51 |

HSV = herpes simplex virus

Skinner et al "Follow-up report on 50 subjects vaccinated against herpes genitalis with Skinner vaccine" Med Micrbiol Immunol (1987) 176:161–168, which shows a significant reduction (from 25% to 2%) in contraction of herpes in vaccinated subjects exposed to infection.

This paper reports the efficacy and safety of vaccination in 50 subjects at high risk of herpes genitalis, followed up for a maximum period of 4 years.

Protocol of Study. Groups of 7, 16 and 27 subjects received one, two or three vaccinations respectively (Table 4). Each vaccine dose was prepared from $2 \times 10^7$ virus-infected cells and contained approximately 300 μg protein; one subject received three vaccinations which each contained 1.5 μg protein ($10^8$ cell equivalents) per vaccine dosage without adjuvant. Vaccinations were administered by subcutaneous inoculation into the posterior aspect of the upper arm. Adjuvant was given with the vaccine course in 44 subjects.

Subjects were followed up alphabetically. The patient was interviewed in depth concerning a possible history of contraction of the disease, evidence of side-effects of vaccination and an assessment made of the degree of exposure to the virus during the follow-up period (see Table 5).

TABLE 3

| Pattern of diseases in 50 index cases | |
| --- | --- |
| Frequency of recurrences per patient per year: | |
| Clinical | 6.2(±1.01) |
| Abortive | 4.8(±0.76) |
| Mean duration (days): | 5.15(±0.41) |
| Mean number of lesions: | 3.5(±0.37) |
| Extent of lesions: | |
| Pinhead | 10 |
| 1 cm | 15 |
| 1 cm | 5 |
| Not known | 10 |
| Pain/discomfort from lesions: | |
| None | 2 |
| Mild | 17 |
| Moderate | 12 |
| Severe | 7 |
| Unbearable | 1 |
| Associated clinical features: | |
| Depression | 32 |
| Lymphadenopathy | 26 |
| Fatigue | 25 |
| Social disruption associated with recurrences: | |
| Retiral to bed | 2 |
| Off work | 1 |
| None | 30 |

TABLE 4

| | | | Vaccination schedules | | | | | |
| --- | --- | --- | --- | --- | --- | --- | --- | --- |
| Number of vaccinations | Number of subjects | Number receiving adjuvants | Vaccine batch | | | | | |
| | | | C | F | G | H | $I_s$ | |
| 1 | 7 | 6 | 1 | 1 | 1 | 2 | 2 | |
| 2 | 27 | 24 | 4 | 0 | 3 | 18 | 2 | |
| 3 | 16 | 14 | 1 | 1 | 2 | 11 | 1 | |
| Total | 50 | 44 | 6 | 2 | 6 | 31 | 5 | |

Inoculation sites were inspected and blood samples withdrawn to investigate levels of immunological reactivity to host cell components in the vaccine. In female subjects cervical swabs were taken where possible and a cervical smear obtained.

Virus isolation. Cervical swabs were obtained from the vagina and suspended in 1 ml phosphate-buffered saline. The suspension was adsorbed to baby hamster kidney cells in suspension and plated out in 5-cm plastic Petri dishes. Samples were considered negative if there was no virus cytopathic effect within 72 h.

TABLE 5

| Sex-related variables in consortships | |
| --- | --- |
| Frequency of sexual intercourse per week | 3.1 |
| Frequency of oro-genital sexual contact per week | 2.9 |
| Method of contraception: | |
| Contraceptive pill | 22 |
| None | 6 |
| Diaphragm | 5 |
| Sterilization | 2 |
| Condom | 1 |
| Frequency of unprotected sexual activity during: | |

TABLE 5-continued

| Sex-related variables in consortships | |
| --- | --- |
| Clinical lesions | |
| never | 31 |
| at least once | 10 |
| Abortive recurrences | |
| never | 20 |
| at least once | 12 |
| Oral cold sores | |
| never | 36 |
| at least once | 1 |

In certain patients information was not available or was considered unreliable and group totals do not summate to 50

Immunological reactivity against MRC-5 antigens and calf serum antigen. Sera were tested by solid-phase radio-immunoassay using $^{125}I$ iodine-labelled protein A. A hyper-immune rabbit anti-MRC cell serum was included as a positive control in every assay. The assay was carried out by a modified method of Skinner GRB, Woodman CBJ, Hartley CE, Buchan A, Fuller A, Durham J. Synno M, Clay JC, Melling J. Wiblin C. Wilkins J (1982) "Preparation and Immunogenicity of Vaccine Ac $NFU_1(S^-)$ MRC Towards the Prevention of Herpes Genitalis, Br. J Vener Dis, 58, 381–386 in round-bottomed flexible, 96-well trays (Flow Laboratories), coated overnight with 50 µl of an appropriate dilution of antigen. The antigen was removed, the trays washed five times with phosphate-buffered saline and non-specific sites blocked with 50 µl of 100% FCS in DA at 37° C. for 1 h. The FCS was removed, the trays rewashed and 50 µl of five-fold dilutions of sera were added to the appropriate well for 1 h. Serum was removed, trays washed and 50 µl of $^{125}I$ protein A containing 200 µl/ml ovalbumin and providing 40,000–50,000 cpm/well was added for 1 h at room temperature. The plate was washed, cut up and counted on a gamma counter. The end-point of each serum was calculated. Sera were recorded as negative when there was no activity at less than a 1:5 dilution.

Cervical cytology. Cytological screening was carried out at a Clinical Research Department of the Birmingham Maternity Hospital. Cervical smears were fixed in 95% ethanol.

Vaccine. Vaccine was prepared as previously described by (Skinner GRB, Buchan A, Williams D, Marsden J, Hartley CE, Wilbanks G, Turyk Namkoong ES (1982), "Immunogenicity and Protective Efficacy in a Rhesus Monkey Model of Vaccine Ac $NFU_1(S^-)$ MRC Against Primary Type 2 Herpes Simplex Virus Infection", Br J. Exp Pathol, 63 378–387) except that whole infected MRC5 cells, instead of disrupted infected cell extract, were treated with Nonidet, permitting removal of cell nuclei prior to further steps in vaccine preparation. In brief, therefore, the vaccine is a detergent-treated, particle-free cytoplasmic extract of type 1 HSV (troisbel)-infected human embryo lung cells (MRC5). The vaccine contained less than 50 pg viral DNA per vaccine dose (0.3 mg protein), with a fragment size of less than 100 bases as determined by agarose gel analysis; the vaccine contains all the polypeptides synthesized by virus-infected cells, including glycoprotein D (gD), which was present at a concentration of at least 0.6 µg per vaccine dose.

RESULTS

Contraction of herpes genitalis. One subject reported features suggestive of contraction of herpes virus infection of the perianal region. The patient was a homosexual male who had an extremely high frequency of sexual contact including active and passive anal intercourse with a large number of partners. Two episodes of "fissuring" or "cracking" in the anal region were adjudged by a medical practitioner at the Special Disease Clinic to be herpetic, although swab on two occasions failed to isolate herpes virus. Although the evidence is not conclusive subjects who have symptoms which suggest contraction of herpes genitalis have been recorded as cases of "failed vaccination". The contraction rate was therefore 1 to 50 subjects over a total follow-up period of 57.8 patient years or 57.8 exposure year units (UYE) with a standard contraction rate (SCR) of $1/57.8 = 0.02$ (see below).

Herpes simplex virus in female genital tract

Cervical cell scrapes were obtained form 8 to 20 female subjects; there was no evidence of herpes simplex virus in the specimens.

Cervical cytology

Cervical cytology was carried out in 12 of the 20 female subjects in the study; 4 subjects were menstruating at the followup visit and 4 subjects declined to have cytology as in 3 of the subjects the procedure had ben carried out within the last 4 months. Cytology was reported as "negative" in all 12 subjects; this includes smears from 5 subjects as follows: (1) "atypical cells" in a poorly fixed smear; (2) "suspicious" mild squamous cell dyskaryosis; (3) mild squamous atypia; (4) mild squamous atypia; (5) one group of mildly atypical aquamous cells. Repeat cytology from these subjects was requested 6-12 months later.

Quantification of exposure risk

Assessing the extent of "virus exposure" from an index case is difficult. Two criteria were used: first, the pattern of herpetic disease int eh index case, where the risk of virus transmission will particularly increase with recurrent episodes, and secondly, the frequency of sexual intercourse with the index case (Table 3 and 5). To help resolve this problem, we have suggested a "unit of year exposure" (UYE). This represents the degree of exposure of a person consorting for 1 year with an index case who has an average pattern of herpetic disease in terms of the criteria which relate to infectiousness: these are frequency, duration and extent of clinical and abortive recurrences, where the patient reported symptoms typically associated with herpetic recurrences but without cutaneous eruptions.

TABLE 6

| Number of subjects | Abnormality at inoculation sites | | | |
|---|---|---|---|---|
| | Vaccine batch | Adjuvant | Time since vaccination (months) | Abnormality |
| 1005 | H | + | 4 | 1 cm lump |
| 1006 | H | + | 2 | 1 cm lump |
| 1025 | H | + | 6 | 1 cm lump |
| 1037 | G | + | 10 | 1 cm lump |
| 1048 | F | + | 36 | 0.2 cm lump |

In out study, the following averages were calculated and used to construct exposure year units and standard contraction rates: frequency of sexual intercourse per week, 3.1; clinical and abortive recurrences (frequency per year), 11(6.2 clinical and 4.8 abortive); duration (days), 5.2; number of lesions, 3.5.

Thus, a subject consorting with an index case for 1 year with these parameters of infectiousness would, by definition, have an exposure of 1 unit (UYE) and the 50 subjects during 1 year would have 50 UYE; as the study lasted 694 "patient months" or 57.8 "patient years" the total exposure risk equals 57.8 UYE with an SCR of 1/57.8, i.e.e. SCR=0.02 for vaccinated subjects.

Side-effects of vaccination

There was no evidence of any general or significant local side-effect in any of the subjects vaccinated.

Inspection of inoculation sites revealed residual granuloma in 5 subjects—a rate of 5 per 109 vaccinations (5%), although we would anticipate that the granulomata in the 4 subjects who were within 1 year of follow-up (Table 6) would disappear. All 5 subjects received vaccination containing 50% Alhydrogel adjuvant and it is our intention to reduce the adjuvant concentration in subsequent studies.

Sera of vaccinated subjects were investigated for evidence of immunological reactivity against MRC5 host cell antigen and calf serum antigen; sera were tested against MRC5-infected cell extract and MRC5 cell "vaccine", which was essentially a vaccine prepared form uninfected MRC5 cells which served to exclude the possibility that the preparatory process might have imparted unusual immunogenic properties to the MRC cell antigens; there was no evidence of immunological reactivity against MRC5 antigen or calf serum antigen in any of the sera.

Skinner et al "Follow-up report on 101 subjects vaccinated with Skinner herpes vaccine" presented at a conference on vaccines for sexually transmitted diseases held at Oxford, England on Apr. 5-7, 1989, and published as the proceeding of that conference in "Vaccines for Sexually Transmitted Diseases" Ed E Meheus and R E Speer, Pub Butterworth, which has findings corresponding to the immediately preceding reference above but reports on a larger number of subjects.

In this instance, one hundred and one subjects considered to be at risk of herpes genitalis were offered preventative vaccination. These subjects had no history of herpes genitalis but had regular sexual partners with a proven history of the disease.

The purpose of this study was to establish

1. The frequency of contraction of herpes genitalis and the extent of exposure to this virus during the period of follow-up.

2. Evidence of side-effects from vaccination or immunological reactivity against host cell components in the vaccine.

Subjects in Study

The demographic features of the subjects under study are shown in Table 1. The average age was 31.8 years, approximately 25% were married, over 80% of the subjects were in social classes III or above and 95% were Caucasian. In summary, the population represented a fairly middle-class white population in early adulthood.

Protocol of Study

One hundred and one subjects received 247 vaccinations (Table 2). Vaccinations were given at 2-4 week intervals into the posterior aspect of the upper arm. Most vaccinations were given with alhydrogel adjuvant; none of the high dosage vaccinations were given the adjuvant.

Subjects were followed-up alphabetically. The patient was interviewed concerning a possible history of contraction of the disease, evidence of side effects and an assessment made of the degree of exposure to the virus during the follow-up period. Inoculation sites were inspected and blood samples withdrawn to investigate immunological reactivity to host cell components in the vaccine; in female subjects, cervical smears were obtained where possible.

Vaccine Preparation

Vaccine was prepared by high multiplicity infection of serum starved MRC5 cells with type 1 HSV strain "troisbel". Nuclei were separated form virus-infected cells by Nonidet treatment of cytoplasmic extract, formalization and removal of virus particles by ultracentrifugation through 20% sucrose. The preparation was further purified by acetone precipitation redissolution and storage as a freeze-dried preparation.

The vaccine contained all the polypeptides including glycoprotein D that were represented in virus-infected cells but was free of virus particles and contained DNA less than 200 bases in size.

Contraction of Herpes Genitalis

One subject who had received the vaccination with adjuvant reported features suggestive of contraction of herpes virus infection of the peri-anal region. The patient was a homosexual male who had a high frequency of sexual contact with multiple episodes of oral-genital sexual contact and both active and passive anal intercourse with multiple partners during the 48 month period since last vaccination. Two episodes of "fissuring" or "cracking" in the anal region were adjudged by a medical practitioner at the special Disease Clinic to be herpetic although swabs on two occasions failed to isolate herpes virus. While the evidence is not conclusive, as we are recording subjects who have clinical or laboratory evidence of contraction of herpes genitalis, we have recorded this case as a "failed vaccination". The contraction rate was therefore 1 in 101 subjects over a total follow-up period of 173.4 "patient years".

Vaginal swabs were obtained from female subjects; there was no evidence of herpes simplex virus in any swab specimens. Cervical cytology was carried out in 12 female subjects in the study; 4 subjects were menstruating at the follow-up visit and 4 subjects declined to have cytology as in three of the subjects the procedure had been carried out within the last 4 months. Cytology was reported as "negative" in these 12 subjects.

quantification of Exposure Risk in Vaccinated Subjects

Certain immutable features of a consortship namely the pattern of herpetic disease in an index case and the sexual behavior in the consortship have been taken to establish average parameters of "exposure risk" (Table 3). The following functions have been defined:

Unit of yearly exposure (U.Y.E.)—this is the degree of exposure during a year for a consort whose partner (index case) has an average pattern of disease and whose consortship has an average pattern of sexual behavior; these averages were calculated form the sample data in this study (Table 3).

Standard contraction rate (S.C.R.)—this is the number of consorts who contract herpes genitalis per unit of exposure. In the study, one subject reported features suggestive of herpetic disease in 173.5 patient years, a standardized contraction rate of 0.006.

Side Effect of Vaccination

The frequency of immediate discomfort, local response and persistence of granulomatous reaction at the vaccination site was recorded (Table 4). Immediate discomfort of any moment did not occur if the vaccine was given with adjuvant. A local reaction to vaccination was recorded in approximately 80% of subjects and was related to the deployment of adjuvant. A granulomatous reaction to adjuvant was identified at 6 months beyond vaccination in there subjects.

There were no systemic side-effects which could reasonably be attributed to vaccination.

The sera of subjects were investigated for immunological reactivity against MRC5 host cell and calf serum antigen. An uninfected MRC cell vaccine was included to exclude the possibility that the preparative process had imparted unusual immunogenic properties to the MRC-5 cell antigens. There was no evidence of immunological reactivity against MRC-5 antigen or calf serum antigen.

TABLE 1

| Demographic features of 101 vaccinated subjects | |
|---|---|
| Sex of subjects | 55 male |
| Age | mean 31.8 yr |
| | range 18-54 |
| Socio-economic group | |
| I/II | 43 |
| III | 50 |
| IV/V | 8 |
| Marital status | |
| single | 61 |
| married | 27 |
| marital dissolution | 13 |

TABLE 2

| Contraction of herpes genitalis in vaccinated subjects | | |
|---|---|---|
| Number of Vaccinations | Number of Subjects | Number contracting herpes genitalis |
| One | 14 | 0 |
| Two | 40 | 1 |
| Three | | |
| Standard Dose | 29 | 0 |
| High Dose | 6 | 0 |
| Four | 12 | 0 |

The standard and high vaccine dose contained 300 μg and 1500μ of protein respectively (2 × 10⁷ cells = approximately 300 μg of protein)

TABLE 3

| Data on consortship contributing to establishment of average risk levels | |
|---|---|
| Pattern of herpes genitalis (mean values) | |
| frequency of recurrences within one year | |
| chronic | 6.5 |
| abortive | 5.4 |
| total | 11.9 |
| duration of recurrences | 5.7 dy |
| number of lesions | 3.4 |
| Frequency of sexual intercourse per week | 3.1 |

TABLE 4

| Vaccination | Side effects of vaccination | | | |
|---|---|---|---|---|
| | Systemic side-effect | Immediate discomfort* | Local side-effect | |
| | | | Reaction at vaccination site within 72 hrs | Granulomatous reaction lasting >6 mth |
| With adjuvant | 0/171 | 0/171 | 84/111 | 3/108 |
| Without adjuvant | | | | |
| standard dose | 0/58 | 16/58 | 0/14 | 0/58 |
| high dose | 0/18 | 10/18 | 3/13 | 0/18 |
| Total | 0/247 | 26/247 | 87/138 | 3/184 |

*Subjects were asked to record the extent of discomfort as 'none' 'mild' 'moderate' 'severe' or 'unbearable'. Discomfort was recorded in the Table if the extent of discomfort was greater than 'mild'.

It has thus been demonstrated that treatment of subjects with a vaccine against HSV1 prepared by the described method will prevent infection with HSV2 which the agent of genital herpes, and will also mitigate the recurrence of attacks in infected persons, As pointed out above, though the specifically described example discloses preparation of a vaccine against Herpes simplex virus, the similar structure and identical method of replication of other herpes viruses provide prima facie evidence that vaccines against those other viruses could be prepared with equal success, which has been confirmed by experimental evidence in preparation of vaccines against varicella zoster virus, cytomegalovirus and bovine mammalitis virus.

What is claimed is:

1. A vaccine against a herpes virus, having as an active constituent an antigen obtained by sequential steps comprising:
   (a) infecting cells with said herpes virus;
   (b) incubating the infected cells;
   (c) separating intact the nuclei of the infected cells from the cytoplasmic fraction thereof;
   (d) contacting said cytoplasmic fraction with a fixing agent to stabilize viral antigenic proteins in said cytoplasmic fraction; and
   (e) separating antigens of said herpes virus from said cytoplasmic fraction, said separated antigens providing the active constituent of said vaccine.

2. A vaccine according to claim 1 wherein said sequential steps include serum deprivation of said cells before infection thereof.

3. A vaccine according to claim 1 wherein the step of separating said antigens is effected by addition to said cytoplasmic fraction of an organic solvent which reacts with water in preference to the proteins in said cells.

4. A vaccine according to claim 1 wherein said herpes virus is a herpes simplex virus.

5. A vaccine according to claim 4 wherein said virus is a herpes simplex type 1 virus.

6. A vaccine according to claim 5 wherein said virus is the Troisbell virus strain.

7. A vaccine according to claim 1 which includes aluminium hydroxide as an adjuvant.

8. A method of providing increased resistance to infection of a human by herpes simplex virus, comprising treating the human with a vaccine according to claim 4.

9. A method according to claim 8 wherein said vaccine contains antigens to herpes simplex type 1.

10. A method according to claim 9 wherein said antigens are derived from the Troisbell virus strain of herpes simplex type 1.

11. A method according to claim 9 for providing increased resistance to infection by herpes simplex type 2.

12. A method of reducing the physical effects resulting from infection of a human by herpes simplex virus, comprising treating the human with a vaccine according to claim 4.

13. A vaccine according to claim 1 wherein the active constituent of said vaccine comprises proteins of molecular weights, in molecular weight units, or $1.8 \times 10^4$ to $2.1 \times 10^4$, $5.5 \times 10^4$ to $6.0 \times 10^4$ $12 \times 10^4$ to $13 \times 10^4$.

14. A vaccine according to claim 13 wherein the active constituent of said vaccine comprises proteins of the Troisbell strain of herpes simplex virus type 1 additionally having molecular weights, in molecular weight units, $8 \times 10^4$ to $9 \times 10^4$ and $3.0 \times 10^4$ to $3.6 \times 10^4$.

15. A vaccine against herpes simplex virus comprising the presence of proteins of the molecular weights shown in FIGS. 1 and 2, said proteins comprising the Troisbell strain of herpes simplex virus 1.

* * * * *

UNITED STATES PATENT AND TRADEMARK OFFICE
CERTIFICATE OF CORRECTION

PATENT NO. : 5,219,567
DATED : June 15, 1993
INVENTOR(S) : Skinner et al.

It is certified that error appears in the above-indentified patent and that said Letters Patent is hereby corrected as shown below:

Claim 13, col. 22, line 42, change "or" to --of--;
line 43, after "$6.0 \times 10^4$" insert --and--.

Claim 14, col. 22, line 48, after "units," insert --of--.

Signed and Sealed this

Eighth Day of February, 1994

Attest:

BRUCE LEHMAN

Attesting Officer         Commissioner of Patents and Trademarks